US010882836B1

United States Patent
Liu et al.

(10) Patent No.: US 10,882,836 B1
(45) Date of Patent: Jan. 5, 2021

(54) METHOD FOR PURIFYING CRUDE 2,5-FURANDICARBOXYLIC ACID COMPOSITION

(71) Applicant: FAR EASTERN NEW CENTURY CORPORATION, Taipei (TW)

(72) Inventors: Shu-Wei Liu, Taipei (TW); Xin-An Lu, Taipei (TW)

(73) Assignee: FAR EASTERN NEW CENTURY CORPORATION, Taipei (TW)

( * ) Notice: Subject to any disclaimer, the term of this patent is extended or adjusted under 35 U.S.C. 154(b) by 0 days.

(21) Appl. No.: 16/736,263

(22) Filed: Jan. 7, 2020

(30) Foreign Application Priority Data

Jul. 2, 2019 (TW) .............................. 108123215 A

(51) Int. Cl.
*C07D 307/68* (2006.01)
(52) U.S. Cl.
CPC .................................. *C07D 307/68* (2013.01)
(58) Field of Classification Search
CPC .................................................. C07D 307/68
See application file for complete search history.

(56) References Cited

FOREIGN PATENT DOCUMENTS

| WO | WO-2016195500 A1 * | 12/2016 | .............. B01J 23/75 |
| WO | WO-2019132663 A1 * | 7/2019 | ........... C07D 307/68 |

OTHER PUBLICATIONS

Byrne, F.P.,"Tools and techniques for solvent selection: green solvent selection guides." Sustainable chemical processes 4.1 (2016): 7:1-24.*

* cited by examiner

*Primary Examiner* — John M Mauro
(74) *Attorney, Agent, or Firm* — MLO, a professional corp.

(57) ABSTRACT

A method for purifying a crude 2,5-furandicarboxylic acid composition including 2,5-furandicarboxylic acid and 2-furoic acid is disclosed. The method includes the steps of: (a) mixing the crude 2,5-furandicarboxylic acid composition with a solvent solution that includes alcohol so as to obtain a mixture; (b) heating the mixture to permit full dissolution of the crude 2,5-furandicarboxylic acid composition in the solvent solution; and (c) cooling the mixture to permit recrystallization of the 2,5-furandicarboxylic acid from the mixture so as to obtain purified 2,5-furandicarboxylic acid.

6 Claims, No Drawings

METHOD FOR PURIFYING CRUDE 2,5-FURANDICARBOXYLIC ACID COMPOSITION

CROSS-REFERENCE TO RELATED APPLICATION

This application claims priority of Taiwanese Patent Application No. 108123215, filed on Jul. 2, 2019.

FIELD

The present disclosure relates to a method for purifying a crude 2,5-furandicarboxylic acid composition, and more particularly to a method for purifying a crude 2,5-furandicarboxylic acid composition that includes 2-furoic acid.

BACKGROUND 2,5-furandicarboxylic acid (FDCA) is a compound that can be produced from biomass without requiring chemical refinement, and thus its production is regarded as adhering to the concepts of green chemistry. FDCA can be used as a bio-based alternative to terephthalic acid, which is a raw material in the production of polyethylene terephthalate (PET). In fact, as compared with PET, polyethylene furanoate (PEF), which is a chemical analogue of PET and is produced from FDCA, exhibits even intrinsically higher gas barrier properties for oxygen, water vapor, carbon dioxide, etc.

Conventionally, the industrial method for synthesizing FDCA which adheres to the concepts of green chemistry, involves catalytic oxidation of furan derivatives (e.g., 5-hydroxymethylfurfural (HMF), 5-(alkoxymethyl)furfural (RMF), etc.) that are produced from the dehydration of saccharides. However, the thus obtained crude FDCA (cFDCA) usually contains impurities of furan derivatives, particularly monocarboxylic acid species such as 2-furoic acid (2-FA). If the cFDCA is not further purified, the impurities of furan derivatives contained therein may cause an undesirable effect of terminating the chain growth of a polymer, resulting in a low polymer viscosity of the thus obtained PEF which may in turn affect the thermoplastic properties thereof.

U.S. Pat. No. 8,969,404 B2 discloses a process for purifying crude FDCA composition by subjecting solvated FDCA composition to hydrogenation reaction so as to form other types of water-soluble furan derivatives, which are then separated from water-insoluble FDCA. However, a high temperature (around 170° C.), a high hydrogen partial pressure and an expensive catalyst such as palladium on carbon (Pd/C), etc. are indispensible in the hydrogenation reaction of the purifying process.

SUMMARY

Therefore, an object of the present disclosure is to provide a method for purifying a crude 2,5-furandicarboxylic acid composition which can alleviate at least one of the drawbacks of the prior art.

According to the present disclosure, the crude 2,5-furandicarboxylic acid composition includes 2,5-furandicarboxylic acid and furan derivatives which contain 2-furoic acid. The method includes the steps of:

(a) mixing the crude 2,5-furandicarboxylic acid composition with a solvent solution that includes alcohol to obtain a mixture;

(b) heating the mixture to permit full dissolution of the crude 2,5-furandicarboxylic acid composition in the solvent solution; and (c) cooling the mixture to permit recrystallization of the 2,5-furandicarboxylic acid from the mixture so as to obtain purified 2,5-furandicarboxylic acid.

DETAILED DESCRIPTION

According to the present disclosure, a method for purifying a crude 2,5-furandicarboxylic acid composition includes the following steps (a) to (c). The crude 2,5-furandicarboxylic acid composition includes 2,5-furandicarboxylic acid and furan derivatives which contain 2-furoic acid.

In step (a), the crude 2,5-furandicarboxylic acid composition is mixed with a solvent solution that includes alcohol to obtain a mixture.

In step (b), the mixture is heated to permit full dissolution of the crude 2,5-furandicarboxylic acid composition in the solvent solution.

In step (c), the mixture is cooled to permit recrystallization of the 2,5-furandicarboxylic acid from the mixture, so as to obtain purified 2,5-furandicarboxylic acid.

Examples of the alcohol may include, but are not limited to, methanol, ethanol, isopropanol, and combinations thereof. In certain embodiments, the alcohol is ethanol.

In certain embodiments, the solvent solution further includes water. In an exemplary embodiment, in the solvent solution, a weight ratio of the alcohol to water ranges from 5:1 to 5:5.

In certain embodiments, in step (b), the mixture is heated to a first temperature ranging from 40° C. to 120° C.

In certain embodiments, in step (c), the mixture is cooled to a second temperature ranging from 0° C. to 30° C.

In certain embodiments, the method further includes, after step (c), a step (d) of removing the 2-furoic acid. In an exemplary embodiment, step (d) includes the sub-steps of: (d1) collecting the purified 2,5-furandicarboxylic acid by filtration; and (d2) drying the purified 2,5-furandicarboxylic acid at a third temperature ranging from 80° C. to 130° C.

The present disclosure will be further described by way of the following examples. However, it should be understood that the following examples are intended solely for the purpose of illustration and should not be construed as limiting the present disclosure in practice.

EXAMPLES

Example 1 (E1)

First, 49.0 g of methanol was added to 1.0 g of a crude 2,5-furandicarboxylic acid (cFDCA) composition that includes 2,5-furandicarboxylic acid (FDCA) and furan derivatives (i.e, approximately 526 ppm of 2-furoic acid (2-FA)) in a container, so as to obtain a mixture. Next, the container was sealed and the mixture was heated to a first temperature of 40° C., which was maintained for 10 minutes to permit full dissolution of the cFDCA composition in the methanol. After that, the heated mixture in the container was cooled to a second temperature of 0° C., which was maintained for 30 minutes, so as to recrystallize FDCA in the mixture. The mixture was subjected to suction filtration so as to remove liquid portion thereof, and then the recrystallized FDCA thus collected was dried at a third temperature of 100° C. to obtain a solid product containing purified FDCA.

Examples 2 to 4 (E2 to E4)

The methods of E2, E3 and E4 were similar in procedure to E1, except that, the amount of methanol used in E2 to E4 were respectively 24.0 g, 15.7 g and 13.3 g, and the first temperature applied in E2 to E4 were 65° C., 80° C. and 95° C., respectively.

Examples 5 and 6 (E5 and E6)

The methods of E5 and E6 were similar in procedure to E1, except that methanol was replaced with ethanol, and the first temperature applied in E5 and E6 were 60° C. and 85° C., respectively.

Examples 7 and 8 (E7 and E8)

The methods of E7 and E8 were similar in procedure to E5, except that, the amount of methanol used in E7 and E8 were respectively 19.0 g and 15.7 g, and the first temperature applied in E7 and E8 were 100° C. and 110° C., respectively.

Example 9 (E9)

First, 39.0 g of a solvent solution (a weight ratio of methanol to water was 5:3) was added to 1.0 g of the crude 2,5-furandicarboxylic acid (cFDCA) composition as described in E1, in a container so as to obtain a mixture. Next, the container was sealed and the mixture was heated to a first temperature of 65° C., which was maintained for 10 minutes, so as to permit full dissolution of the cFDCA composition in the solvent solution. After that, the heated mixture in the container was cooled to a second temperature of 0° C., which was maintained for 30 minutes, so as to recrystallize FDCA in the mixture. The mixture was subjected to suction filtration so as to remove liquid portion thereof, and then the recrystallized FDCA thus collected was dried at a third temperature of 100° C. to obtain a solid product containing purified FDCA.

Example 10 (E10)

The method of E10 was similar in procedure to E9, except that the amount of the solvent solution was 24.0 g, and the first temperature was 80° C.

Examples 11 and 12 (E11 and E12)

The methods of E1 and E12 were similar in procedure to E9, except that in E11 and E12, methanol in the solvent solution was replaced with ethanol and a weight ratio of ethanol to water was 5:3. In addition, the first temperature applied in E1 and E12 were 60° C. and 75° C., respectively.

Example 13 (E13)

The method of E13 was similar in procedure to E11, except that the amount of solvent solution was 15.7 g, and the first temperature was 88° C.

Examples 14 to 17 (E14 to E17)

The methods of E14 to E17 were similar in procedure to E13, except that, in E14 to E17, the weight ratio of ethanol to water in the solvent solution were 5:1, 5:2, 5:4 and 5:5, respectively, and the first temperature were 90° C., 85° C., 90° C. and 93° C., respectively.

Comparative Examples 1 and 2 (CE1 and CE2)

The methods of CE1 and CE2 were similar in procedure to E8, except that in CE1 and CE2, methanol was replaced with water, and the first temperature were 90° C. and 170° C., respectively. In addition a container used in CE2 is capable of withstanding a high temperature.

Determination of 2-FA Removal Percentage and FDCA Percentage Purity

In order to determine 2-FA and FDCA contents, the cFDCA composition before purification, and each of the solid products obtained by the methods of E1 to E17 and CE1 and CE2 were respectively dissolved in methanol and then subjected to high-performance liquid chromatography analysis (column type: C18 from Waters; mobile phase: acetonitrile and 0.05% phosphoric acid solution (10%:90%, v/v) in an elution gradient shown in Table 1 below).

TABLE 1

| Time (min) | Acetonitrile (v %) | 0.05% Phosphoric acid solution (v %) |
|---|---|---|
| 0.0 | 10 | 90 |
| 5.0 | 10 | 90 |
| 6.0 | 30 | 90 |
| 13.0 | 50 | 50 |
| 14.5 | 100 | 0 |
| 16.0 | 100 | 0 |

2-FA removal percentage was calculated using the formula: $[1-(A/B)] \times 100\%$, in which A represents the 2-FA content (ppm) in the purified solid product, and B represents the 2-FA content (ppm) in the cFDCA composition. FDCA percentage purity was calculated using the formula: $(C/D) \times 100\%$, in which C represents the weight of FDCA in the purified solid product, and D represents the total weight of the purified solid product. The results were shown in Table 2 below.

TABLE 2

|  | 2-FA removal percentage (%) | FDCA percentage purity (%) |
|---|---|---|
| E1 | 85 | 99.9 |
| E2 | 81 | 99.8 |
| E3 | 69 | 99.7 |
| E4 | 55 | 99.5 |
| E5 | 92 | 99.8 |
| E6 | 92 | 99.8 |
| E7 | 88 | 99.7 |
| E8 | 81 | 99.8 |
| E9 | 88 | 99.8 |
| E10 | 80 | 99.7 |
| E11 | >99 | 99.8 |
| E12 | >99 | 99.9 |
| E13 | >99 | 99.9 |
| E14 | 91 | 99.8 |
| E15 | 94 | 99.9 |
| E16 | 96 | 99.9 |
| E17 | 88 | 99.8 |
| CE1 | 7 | 99.2 |
| CE2 | >99 | 99.9 |

As shown in Table 2, in each of E1 to E17, the 2-FA removal percentage is higher than 55%, and the percentage purity of FDCA is higher than 99.5%, indicating that 2-FA was effectively removed from the cFDCA composition, thereby obtaining a highly purified FDCA. In contrast, the 2-FA removal percentage in CE1 is merely 7%, and the FDCA percentage purity is 99.2%, indicating that effective removal of 2-FA during purification of cFDCA composition was not achieved, and a highly purified FDCA cannot be obtained by the method of CE1. Although a high 2-FA removal percentage and a high FDCA percentage purity may be achieved in CE2, complete dissolution of the cFDCA composition in the solvent solution is required to be conducted at a relatively high temperature (i.e., 170° C.).

In summary, by virtue of the method for purifying cFDCA composition of the present disclosure, which utilizes simple procedures and mild conditions, furan derivatives such as 2-FA, can be effectively removed, thereby obtaining FDCA with high purity.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, FIGURE, or description thereof for the purpose of streamlining the present disclosure and aiding in the understanding of various inventive aspects, and that one or more features or specific details from one embodiment may be practiced together with one or more features or specific details from another embodiment, where appropriate, in the practice of the disclosure.

While the present disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for purifying a crude 2,5-furandicarboxylic acid composition, which includes 2,5-furandicarboxylic acid and 2-furoic acid, the method comprising the steps of:
   (a) mixing the crude 2,5-furandicarboxylic acid composition with a solvent solution that includes alcohol and water present in a weight ratio ranging from 5:1 to 5:5 to obtain a mixture;
   (b) heating the mixture to permit full dissolution of the crude 2,5-furandicarboxylic acid composition in the solvent solution; and
   (c) cooling the mixture to permit recrystallization of the 2,5-furandicarboxylic acid from the mixture, so as to obtain purified 2,5-furandicarboxylic acid.

2. The method as claimed in claim 1, wherein the alcohol is selected from the group consisting of methanol, ethanol, isopropanol, and combinations thereof.

3. The method as claimed in claim 1, wherein in step (b), the mixture is heated to a first temperature ranging from 40° C. to 120° C.

4. The method as claimed in claim 1, wherein in step (c), the mixture is cooled to a second temperature ranging from 0° C. to 30° C.

5. The method as claimed in claim 1, wherein step (c) includes:
   recrystallizing the 2,5-furandicarboxylic acid from the mixture; and
   separating the 2-furoic acid in the mixture from the 2,5-furandicarboxylic acid.

6. The method as claimed in claim 5, wherein separating the 2-furoic acid in the mixture from the 2,5-furandicarboxylic acid includes collecting the purified 2,5-furandicarboxylic acid by filtration, and then drying the purified 2,5-furandicarboxylic acid at a third temperature ranging from 80° C. to 130° C.

\* \* \* \* \*